US008227427B2

(12) United States Patent
Coracci Neto et al.

(10) Patent No.: US 8,227,427 B2
(45) Date of Patent: Jul. 24, 2012

(54) VETERINARIAN COMPOSITION COMPRISING AN ORGANIC SALT OF LEVAMISOLE IN COMBINATION WITH AT LEAST ONE AVERMECTIN AND/OR MILBEMYCIN

(75) Inventors: Dolivar Coracci Neto, Sertaozinho (BR); Nelson Henriques Fernandes Filho, Jaboticabal (BR); Ricardo da Silva Sercheli, Jaboticabal (BR)

(73) Assignee: NPA—Nucleo de Pesquisas Aplicadas Ltda., Jaboticabal (BR)

( * ) Notice: Subject to any disclaimer, the term of this patent is extended or adjusted under 35 U.S.C. 154(b) by 575 days.

(21) Appl. No.: 12/097,683

(22) PCT Filed: Dec. 18, 2006

(86) PCT No.: PCT/BR2006/000282
§ 371 (c)(1),
(2), (4) Date: Nov. 3, 2008

(87) PCT Pub. No.: WO2007/068073
PCT Pub. Date: Jun. 21, 2007

(65) Prior Publication Data
US 2009/0075918 A1    Mar. 19, 2009

(51) Int. Cl.
*A61K 31/70* (2006.01)
*A61K 31/425* (2006.01)

(52) U.S. Cl. .......................... 514/27; 514/368
(58) Field of Classification Search ................. 513/7.1; 548/155; 514/27, 368
See application file for complete search history.

(56) References Cited

FOREIGN PATENT DOCUMENTS

| BR | PI0505716 A | 9/2007 |
|---|---|---|
| GB | 2150024 A | 6/1985 |
| WO | 00/74489 A1 | 12/2000 |
| WO | 2004/009080 A1 | 1/2004 |

OTHER PUBLICATIONS

International Search Report.
Analytical Report Characterization of Pharmaceutical Input Aurixazol (Feb. 20, 2010).

*Primary Examiner* — Elli Peselev
(74) *Attorney, Agent, or Firm* — Laurence P. Colton; Smith Risley Tempel Santos LLC

(57) ABSTRACT

Veterinarian composition comprising an organic salt of levamisole in combination with at least one avermectin and/or milbemycin. A veterinarian formulation comprising of organics salts of levamisole, more specifically to the levamisole salt of 2,6-diiodo-4-nitrophenol and the levamisole salt of 4-hydroxy-3-iodo-5-nitrobenzonitrile with avermectins and milbemycins and its use in treatment of helminthiasis in mammals, in particular in bovines, swines, caprines, equines, ovines, canines and felines.

13 Claims, No Drawings

VETERINARIAN COMPOSITION COMPRISING AN ORGANIC SALT OF LEVAMISOLE IN COMBINATION WITH AT LEAST ONE AVERMECTIN AND/OR MILBEMYCIN

STATEMENT OF RELATED APPLICATIONS

This patent application is the United States PCT Chapter II National Phase of PCT/BR2006/000282, having an International Filing Date of 18 Dec. 2006, which claims priority on Brazilian Patent Application No. PI 0506279-9, having a filing date of 16 Dec. 2005, both of which are incorporated herein by this reference in their entireties.

BACKGROUND OF THE INVENTION

The association of different classes of substances presenting antihelminthic actions aims to combat an increasing resistance of parasites to most of the drugs used. The resistance of parasites to different classes of antihelminthic drugs has been reported since early use of these drugs. The resistance for benzimidazole is all over the world. Studies have been reported, mainly related to three main species of bovine's parasites: *Ostertagia, Trichostrongylus, Cooperia*. Although parasites resistance to levamisole is well known, it is much more restrict than to benzimidazoles. Resistance and crossed resistance reports have been reported, mainly to *Cooperia* species.

The strategy to combat this resistance has been trying to avoid the indiscriminate use of antihelminthic drugs, to alternate drugs during treatment and to use potential number of parasites which survive the treatment. The association of active principles aiming a synergetic function among them is a well known strategy, mainly in the treatment of pathogenic agents with bacteria, protozoans, fungus, and parasites. A real synergism occurs when the association of two or more pharmaceutical actives is higher than all individual actions together.

The aim of this invention is to describe the use of organic salts of levamisole associated to avermectins and/or milbemycins in the combat to helminthiasis.

Levamisole (L-2,3,5,6-tetrahydro-6-phenil-imidazo-[2,1-b]thiazole), it is an antiparasitary widely used for intestinal control of nematodes and respiratory worms in some animals. Due to its basic characteristic, it forms salts with organic and inorganic acids, depending on $pk_a$ of this acid.

Antiparasitaries such as disophenol (2,6-dilodo-4-nitrophenol) and nitroxinil (4-hydroxy-3-iodo-5-nitrobenzonitrile), which are used to control trematodes and some nematodes, produce a salt with levamisole under some conditions due to its acid characteristic of phenol group of these molecules. The description, obtainment, and use of levamisole salt of 4-hydroxy-3-iodo-5-nitrobenzonitrile were described in the patent GB 2150024 A. Levamisole salt of 2,6-diiodo-4-nitrophenol and levamisole salt of 4-hydroxy-3-iodo-5-nitrobenzonitrile from now on will be referred only as levamisole organic salts, when suitable.

Avermectins, a compound which belongs to macrocyclic lactones, are powerful antiparasitary agents which are used to combat parasites in mammals. They are secondary metabolic produced by *Streptomyces avemitilis*, obtained through a fermenting process. Some avermectins are obtained in a semi synthetic composition as ivermectin, which is obtained through abamectin hydrogenization. A series of compounds denominated avermectins are abamectin, doramectin, eprinomectin, ivermectin and selamectin.

Milbemycins are similar to avermectins in their structure, because they have a 16 membered ring structures. However, it does not have a disaccharidic sub unit and there are constituent differences. Milbemycin used in the association are selected from the group consisting of moxidectin, milbemycin and milbemycin oxime.

Considering these aspects, it is known that levamisole salt of 2,6-diiodo-4-nitrophenol, as well as levamisole salt of 4-hydroxy-3-iodo-5-nitrobenzonitrile, both combine the action of levamisole against nematodes, for example, *Haemonchus contortus, Ostertagia* spp., *Trichostrongylus* spp. (example: *Trichostrongylus axei*), *Cooperia* spp. (*Cooperia oncophora*), *Nematordirus* spp. (example: *Oesaphagostomum venulosum*), *Strongyloides* spp. (example: *Strongyloides papillosus*), *Bunostomum* spp. (ex: *Bunostomum trigonocephalum*), *Chabertia* spp (ex: *Chabertia ovina*), *Trichuris* spp. (ex: *Trichuris ovis*) and *Dictyocaulus* spp. (ex: *Dictyocaulus filaria* and *Dictyocaulus viviparous*) with the action of disophenol or nitroxinil against trematodes, for example, *Fasciola hepatic* and gigantic *Fasciola*, and some nematodes, for example, *Haemonchus contortus, Bunostomum* spp. *Oesaphagostomum* spp., *Parafilaria bovicola*. Considering that levamisole presents a low action against *Ostertagia* parasites and a good action against *Cooperia* class, and avermectins and milbemycin has a good inverse action, which means low action against *Cooperia* and good action against *Ostertagia*, a combination of actions of levamisole salt of 2,6-diiodo-4-nitrophenol and levamisole salt of 4-hydroxy-3-iodo-5-nitrobenzonitrile with avermectins and milbemycins, aiming a wide spectrum formulation against parasites, besides a synergism of actions among actives. In such case, this association maybe indicated as a parasiticide in the treatment of nematodes, cestodes, and trematodes in bovines, swine, caprines, equines, ovines, canines and felines.

Associations of avermectins and levamisole have already been described before, in patent WO 00061068 and in patent application WO 2004/009080 A1. The greatest discovery in the study is the use of salts of levamisole, which besides levamisole action they present fascioliscide action, when associated with avermectins. Other associations with fascioliscide compounds were proposed in documents WO 95/05812 and GB 2386067A, both describing the association of avermectins and milbemycins with closantel.

BRIEF SUMMARY OF THE INVENTION

This invention is a veterinarian pharmaceutical formulation which presents fascioliscide action and a potent action against nematodes, cestodes, trematodes. This invention also is a new veterinarian pharmaceutical product presenting the association of organic salts of levamisole with avermectins and milbemycins. This invention also is an association of levamisole salt of 2,6-diiodo-4-nitrophenol with avermectins and milbemycins for antiparasitary agent.

This invention presents new veterinarian products from the association of avermectins and milbemycins with other antiparasitary agents, such as organic salts of levamisole.

Levamisole organic salts used in this invention are of levamisole salt of 4-hydroxy-3-iodo-5-nitrobenzonitrile and levamisole salt of 2,6-diiodo-4-nitrophenol.

Avermectins and milbemycins used in this invention are abamectin, ivermectin, doramectin, eprinomectin, selamectin, moxidectin, milbemycin and milbemycin oxime.

The used dosage will depend on the helminthes' nature, the animal which will be treated and administration route. Levamisole salt of 4-hydroxy-3-iodo-5-nitrobenzonitrile can range from 1 to 50 mg per kilogram of body weight, preferably from 5 to 15 mg per kilogram of body weight, considering that dosage of 7.2 mg/kg of body weight brings satisfactory results in the control of parasites. Levamisole salt of 2,6-diiodo-4-nitrophenol can range from 1 to 50 mg per kilogram of body weight, considering that a dosage of 8.9 mg/kg of body weight generally brings satisfactory results in the control of parasites. Avermectins and milbemycins dosages range from 5 to 500 µg of the active per kilogram of weight, preferably from 50 to 350 µg of the active per kilogram of body weight, considering that a dosage of 200 µg/kg of body weight generally has satisfactory results in the control of parasites.

The pharmaceutical formulations, according to this invention, can be used to administrate the associations of levamisole organic salts with milbemycins and/or avermectins in order to kill internal parasites, such as, nematodes, cestodes, trematodes and fasciola, parasites in animals such as bovines, swines, caprines, felines, canines, equines; according to the dosages and purposes presented in this study specifically for these associations.

The associations are rather done among levamisole organic salt and avermectins or milbemycins. For example, the association of levamisole salt of 4-hydroxy-3-iodo-5-nitrobenzonitrile with abamectin in a parentheral veterinarian formulation. These can be free associations with the use of one or more levamisole organic salts and one or more avermectins or milbemycins, or the mix of them.

What is claimed is:

1. A veterinarian composition comprising an organic salt of levamisole having the formula 2,6-diiodo-4-nitrophenol in combination with avermectins, milbemycins, or combinations thereof, wherein the composition has fasciolicide activity.

2. The veterinarian composition according to claim 1, wherein said avermectins and milbemycins are selected from the group consisting of abamectin, ivermectin, doramectin, eprinomectin, selamectin, moxidectin, milbemycin, milbemycin oxime, and mixtures thereof.

3. The veterinarian composition according to claim 1, wherein the composition comprises the levamisole salt of 2,6-diiodo-4-nitrophenol in dosages ranging from 20-80% in weight of the levamisole salt of 2,6-diiodo-4-nitrophenol.

4. The veterinarian composition according to claim 1, wherein the composition further comprises levamisole salt of 4-hydroxy-3-iodo-5-nitrobenzonitrile.

5. The veterinarian composition according to claim 1, comprising the levamisole salt of 2,6-diiodo-4-nitrophenol in dosages ranging from 1 to 50 mg per kg of body weight.

6. The veterinarian composition according to claim 5, comprising the levamisole salt of 2,6-diiodo-4-nitrophenol in dosages ranging from 5 to 15 mg per kg of body weight.

7. The veterinarian composition according to claim 4, comprising the levamisole salt of 4-hydroxy-3-iodo-5-nitrobenzonitrile in dosages ranging from 1 to 50 mg per kg of body weight.

8. The veterinarian composition according to claim 4, comprising the levamisole salt of 4-hydroxy-3-iodo-5-nitrobenzonitrile in dosages ranging from 5 to 15 mg per kg of body weight.

9. The veterinarian composition according to claim 4, comprising the levamisole salt of 4-hydroxy-3-iodo-5-nitrobenzonitrile in dosages of 8.9 mg per kg of body weight.

10. The veterinarian composition according to claim 1, wherein the avermectins and/or milbemycins are in dosages ranging from 5 to 500 µg of active per kilogram of body weight.

11. The veterinarian composition according to claim 1, wherein the avermectins and/or milbemycins are in dosages ranging from 5 to 350 µg of active per kilogram of body weight.

12. The veterinarian composition according to claim 1, wherein the avermectins and/or milbemycins are in dosages of 200 µg of active per kilogram of body weight.

13. The veterinarian composition according to claim 4, wherein the levamisole salt of 4-hydroxy-3-iodo-5-nitrobenzonitrile is present in dosages ranging from 20-80% by weight of the levamisole salt of 4-hydroxy-3-iodo-5-nitrobenzonitrile.

* * * * *

UNITED STATES PATENT AND TRADEMARK OFFICE
CERTIFICATE OF CORRECTION

| | | |
|---|---|---|
| PATENT NO. | : 8,227,427 B2 | Page 1 of 1 |
| APPLICATION NO. | : 12/097683 | |
| DATED | : July 24, 2012 | |
| INVENTOR(S) | : Dolivar Coraucci Neto, Nelson Henriques Fernandes Filho and Ricardo da Silva Sercheli | |

It is certified that error appears in the above-identified patent and that said Letters Patent is hereby corrected as shown below:

Title Page,

On the Bibliographic page, paragraph (75) Inventors, "Dolivar Coracci Neto" should be changed to --Dolivar Coraucci Neto--.

Signed and Sealed this
Eighteenth Day of September, 2012

David J. Kappos
*Director of the United States Patent and Trademark Office*